United States Patent [19]

Marciel

[11] Patent Number: Plant 7,637

[45] Date of Patent: Sep. 3, 1991

[54] MINIATURE POT ROSE NAMED DEVECLIPSAR

[75] Inventor: Stanley G. Marciel, Aptos, Calif.

[73] Assignee: DeVor Nurseries, Inc., Watsonville, Calif.

[21] Appl. No.: 529,315

[22] Filed: May 29, 1990

[51] Int. Cl.[5] ..... A01H 5/00

[52] U.S. Cl. ..... Plt./7

[58] Field of Search ..... Plt. 7

*Primary Examiner*—James R. Feyrer

*Attorney, Agent, or Firm*—Charles W. Rummler

[57] ABSTRACT

A new and distinct variety of miniature pot rose particularly distinguished by its continuous and profuse production of medium size blooms having broad, closely imbricated petals particularly distinguished by wide greyed purple margins fading inwardly through red purple to surround the broad petal body has a clean Orient Pink coloration, thus providing an unusual flower, the dark and startling petal margins of which render the color of the flower body to appear almost white. This new pot plant rose is also characterized by its profuse and continuous production of flowers above a moderately abundant amount of foliage on a sturdy plant having a height of about 20 cm. which makes it particularly suitable as a pot plant.

1 Drawing Sheet

BACKGROUND OF THE NEW PLANT

This new and distinct variety of pot rose plant originated as a seedling hybrid developed by me at Pleasanton, Calif. by crossing the rose variety 'Scarlet Sunblaze' (unpatented) with pollen from an unnamed and unpatented seedling selected from my collection of rose plants with the object of producing new varieties of well balanced, profusely blooming varieties for 4 inch pot culture and this seedling of the said hybrid was selected for propagation because of the very startling and distinctive coloration of its flowers the petals of which are normally a clear Orient Pink color. This seedling was propagated by me at Pleasanton, Calif. by means of cuttings and the result was so pleasingly successful that, under my direction, propagation of this plant new plant was carried on at my Pleasanton nursery through several successive generations which proved conclusively that the new and distinctive features of my new plant would hold true from generation to generation and appeared to be firmly fixed.

DESCRIPTION OF THE DRAWING

My new miniature pot rose development is illustrated by the accompanying full color photographic drawing which shows my invention as a mature pot plant in full bloom with flowers in several stages of maturity and with a color rendition that is as nearly true as is reasonably possible to obtain by conventional photographic procedures.

DESCRIPTION OF THE NEW VARIETY

The following is a detailed description of my new miniature pot plant as observed in greenhouse at Watsonville, Calif. with the color designations according to the R.H.S. Colour Chart published by The Royal Horticultural Society of London, England.

THE PLANT

Origin: Seedling.

Parentage:

*Seed parent.*—An unpatented variety named 'Scarlet Sunblaze'.

*Pollen parent.*—An unnamed and unpatented seedling from my collection of rose plants maintained for breeding purposes.

Classification:

*Botanic.*—Hybrid miniature rose.

*Commercial.*—Miniature pot rose.

Form: An upright free branching bush.

Height: About 20 cm. at twelve weeks of age in a 4 inch pot.

Main stem length: About 146 mm. from the last flower cut.

*Color.*—Yellow Green 146-A.

Growth habit: Vigorous, sturdy and upright.

Branching character: Free branching.

Foliage:

*Quantity.*—Moderately abundant.

*Number of leaves.*—7 or 8 from the last flower cut. Size: About 76 mm. long, in average.

Leaflets:

*Number.*—3 or 5.

*Size.*—About 20 mm. long and 16 mm. wide, in average.

*Shape.*—Ovate with denticulate margins.

*Texture.*—Leathery and smooth.

*Aspect.*—Glossy.

*Color.*—Upper side — Green 137-B. Under side — Yellow Green 147-B.

*Stiuples.*—Hairy adnate.

*Rachis.*—About 21 mm. long on a 3 part leaf and about 30 mm. long on a 5 part leaf.

Ribs and veins: Depressed on upper side, protruding and rounded on underside.

Thorns:

*Size.*—About 5 mm.

*Color.*—Greyed Orange 176-B.

THE FLOWER

Blooming habit: Continuous and profusely the year around under greenhouse conditions.

Size of bloom: Medium.

*Diameter.*—About 6 cm.

*Depth.*—About 3 cm.

Borne: Singly on strong upright stems.

Shape:

*When bloom first opens.*—Cup shaped.

*When bloom matures.*—Somewhat flattened and nicely imbricated.

Petalage:

*Number.*—34.

*Number of florets.*—11.

*Arrangement.*—Imbricated.

*Form.*—Ovate and slightly dished and with entire margins.

*Texture.*—Soft.

*Appearance.*—Velvety.

*Color.*—Outer petals: Upper side body — generally Orient Pink 36-D with wide margins of Greyed Purple 187-A fading into the body through red purple 60-B and with a base of Yellow 2-D. Reverse side body — Red Purple 60-B surrounded by Orient Pink 36-D with petal margin of Greyed Purple 87-A and base of Yellow 2-D. Inside petals: Upper side body — generally Orient Pink 36-D with margin of Greyed Purple 87-A fading into the body through Red Purple 60-B. Reverse side body — center of Red Purple 60-B surrounded by Orient Pink 36-D and a wide margin of 187-A and petal base of Yellow 2-C.

Petaloids:

*Number.*—11.

*Size.*—About 8 mm.

*Color.*—Mainly Orient Pink 36-D with margin of Red Purple 60-A slightly tinted with Greyed Purple 187-A.

Peduncle:

*Length.*—About 47 mm.

*Color.*—Yellow Green 144-D.

*Character.*—Upright and sturdy for mini-flora.

Discoloration after full bloom: Margins fade from Red Purple 60-B to Red Purple 63-A.

Fragrance: Almost none.

Persistance: The flowers hang on and dry.

Disease resistance: Moderately resistant to mildew, rust and black spots as observed at Watsonville, Calif.

Lasting quality: Long lasting on plant and moderate lasting as a cut flower.

THE REPRODUCTIVE ORGANS

Stamens:

*Number.*—62.

*Arrangement.*—Antrorse.

*Anthers.*—Size: About 3 mm. Color: Yellow Orange 20-B.

*Filaments.*—Length: About 3 mm. Color: Orange 18-D.

*Pollen.*—Color: Yellow Orange 20-B.

Pistils:

*Number.*—56.

*Styles.*—Length: About 7 mm. Color: Greyed Purple 185-C with Green-White 157-C.

*Stigmas.*—Color: Orange 29-D.

Character of the ovaries: Small, slender and covered with silvery hairs.

I claim:

1. The new and distinct variety of miniature pot rose, substantially as herein shown and described, particularly characterized by its profuse and continuous production of medium size flower of a generally Orient Pink petal body coloration with each petal body surrounded by a relatively wide margin of Greyed Purple which fades through Red Purple into the Orient Pink of each petal body, and the petals being closely imbricated, the flowers being borne singly on strong erect stems of a sturdy bush with moderately abundant foliage.

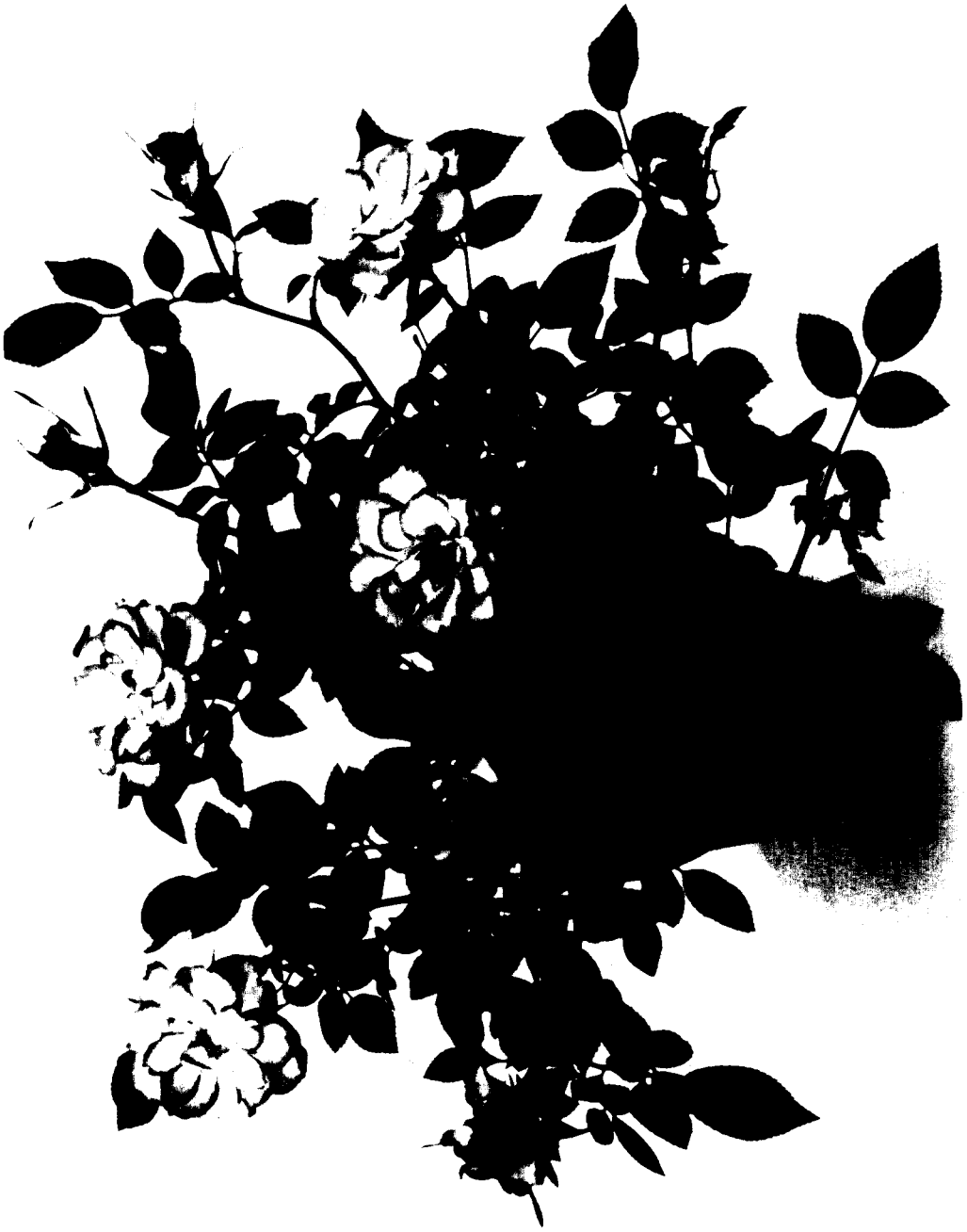

* * * * *